United States Patent
Knoll et al.

(10) Patent No.: US 8,657,620 B2
(45) Date of Patent: Feb. 25, 2014

(54) CONNECTOR ASSEMBLY HAVING A CABLE CLAMP COUPLED TO A COLLET INCLUDING AN ARBOR

(75) Inventors: Wolfgang Knoll, Zipf (AT); Reinhold Bruesite, Zipf (AT); Erich Birglehner, Zipf (AT); Christian Heinrich, Zipf (AT); Christian Holl, Zipf (AT)

(73) Assignee: General Electric Company, Schenectady, NY (US)

( * ) Notice: Subject to any disclaimer, the term of this patent is extended or adjusted under 35 U.S.C. 154(b) by 195 days.

(21) Appl. No.: 13/334,294

(22) Filed: Dec. 22, 2011

(65) Prior Publication Data
US 2013/0165794 A1 Jun. 27, 2013

(51) Int. Cl.
*H01R 13/58* (2006.01)
(52) U.S. Cl.
USPC .......................................... 439/460
(58) Field of Classification Search
USPC ................... 439/449–462, 807–812; 600/459
See application file for complete search history.

(56) References Cited

U.S. PATENT DOCUMENTS

| | | | |
|---|---|---|---|
| 4,664,464 A * | 5/1987 | Hutter et al. | 439/460 |
| 6,142,947 A | 11/2000 | Tran et al. | |
| 8,062,040 B2 | 11/2011 | Konkle et al. | |
| 2007/0159278 A1 | 7/2007 | Aemisegger | |
| 2010/0186989 A1 | 7/2010 | Alvelo et al. | |
| 2011/0312210 A1 * | 12/2011 | Chawgo et al. | 439/460 |
| 2011/0312211 A1 * | 12/2011 | Natoli | 439/460 |
| 2012/0129384 A1 * | 5/2012 | Van Swearingen | 439/449 |

* cited by examiner

*Primary Examiner* — Chandrika Prasad
(74) *Attorney, Agent, or Firm* — The Small Patent Law Group; Dean D. Small

(57) ABSTRACT

A connector assembly for coupling a coaxial cable to an ultrasound probe includes a cable clamp having an opening extending therethrough, the opening sized to receive a coaxial cable therethrough, the coaxial cable including a strain member and a plurality of coaxial cables extending therethrough, and a collet configured to couple to the cable clamp, the collet including an arbor that is configured to tension the strain member to a predetermined tension. A method of fabricating a connector assembly and an ultrasound imaging system are also described herein.

20 Claims, 9 Drawing Sheets

_US 8,657,620 B2_

CONNECTOR ASSEMBLY HAVING A CABLE CLAMP COUPLED TO A COLLET INCLUDING AN ARBOR

BACKGROUND OF THE INVENTION

The subject matter disclosed herein relates generally to ultrasound imaging systems, and more particularly, to a method and apparatus for connecting an ultrasound probe to an ultrasound imaging system.

Ultrasound systems typically include ultrasound scanning devices, such as, ultrasound probes having different transducers that allow for performing various different ultrasound scans (e.g., different imaging of a volume or body). The ultrasound probes are typically connected to an ultrasound system for controlling the operation of the probes. The probes include a scan head having a plurality of transducer elements (e.g., piezoelectric crystals), which may be arranged in an array. The ultrasound system drives the transducer elements within the array during operation, such as, during a scan of a volume or body, which may be controlled based upon the type of scan to be performed. The ultrasound system includes a plurality of channels for communicating with the probe. For example, the channels may transmit pulses for driving the transducer elements and for receiving signals therefrom.

The ultrasound system communicates with and controls the ultrasound probe to control the operation of the transducer elements within the ultrasound probe via a flexible cable. The flexible cable may include, for example, a plurality of (coaxial cables) that couple the transducer elements to the ultrasound system. In operation, the flexible cable experiences different torsional strains that are caused by the operator when moving the ultrasound probe to perform the ultrasound scans. More specifically, the flexible cable may be subjected to flexure-induced stresses that are concentrated at a point where the flexible cable exits the ultrasound probe. As a result, the coaxes may be subjected to stresses that are concentrated at the point where the flexible cable exits the ultrasound probe. The concentrated forces may cause cable fatigue that may result in the breakage of at least some of the coaxes within the flexible cable.

To facilitate reducing theses stresses strain relief devices may be used. However, conventional strain relief devices are typically designed to be utilized with a specific cable. As a result, it may be difficult, for example, for a hospital to maintain and repair a variety of different ultrasound probes.

BRIEF DESCRIPTION OF THE INVENTION

In one embodiment, a connector assembly for coupling an coaxial cable to an ultrasound probe is provided. The connector assembly includes a cable clamp having an opening extending therethrough, the opening sized to receive a coaxial cable therethrough, the coaxial cable including a strain member and a plurality of coaxial cables extending therethrough, and a collet configured to couple to the cable clamp, the collet including an arbor that is configured to tension the strain member to a predetermined tension.

In another embodiment, a method of fabricating a coaxial cable assembly is provided. The method includes inserting a coaxial cable through a cable clamp, the coaxial cable including a strain member and a plurality of coaxial cables extending therethrough, inserting the coaxial cable through a collet, the collet including an arbor, coupling the collet to the cable clamp, coupling the strain member to the arbor, and .rotating the arbor to tension the strain member to a predetermined tension.

In a further embodiment, an ultrasound imaging system is provided. The ultrasound imaging system includes an ultrasound probe, a system cable coupled between the ultrasound probe and a host system, and a connector assembly for coupling the ultrasound probe to the system cable. The connector assembly includes a cable clamp having an opening extending therethrough, the opening sized to receive the system cable therethrough, the system cable including a strain member and a plurality of coaxial cables extending therethrough, and a collet configured to couple to the cable clamp, the collet including an arbor that is configured to tension the strain member to a predetermined tension.

DETAILED DESCRIPTION OF THE INVENTION

Figure 1:
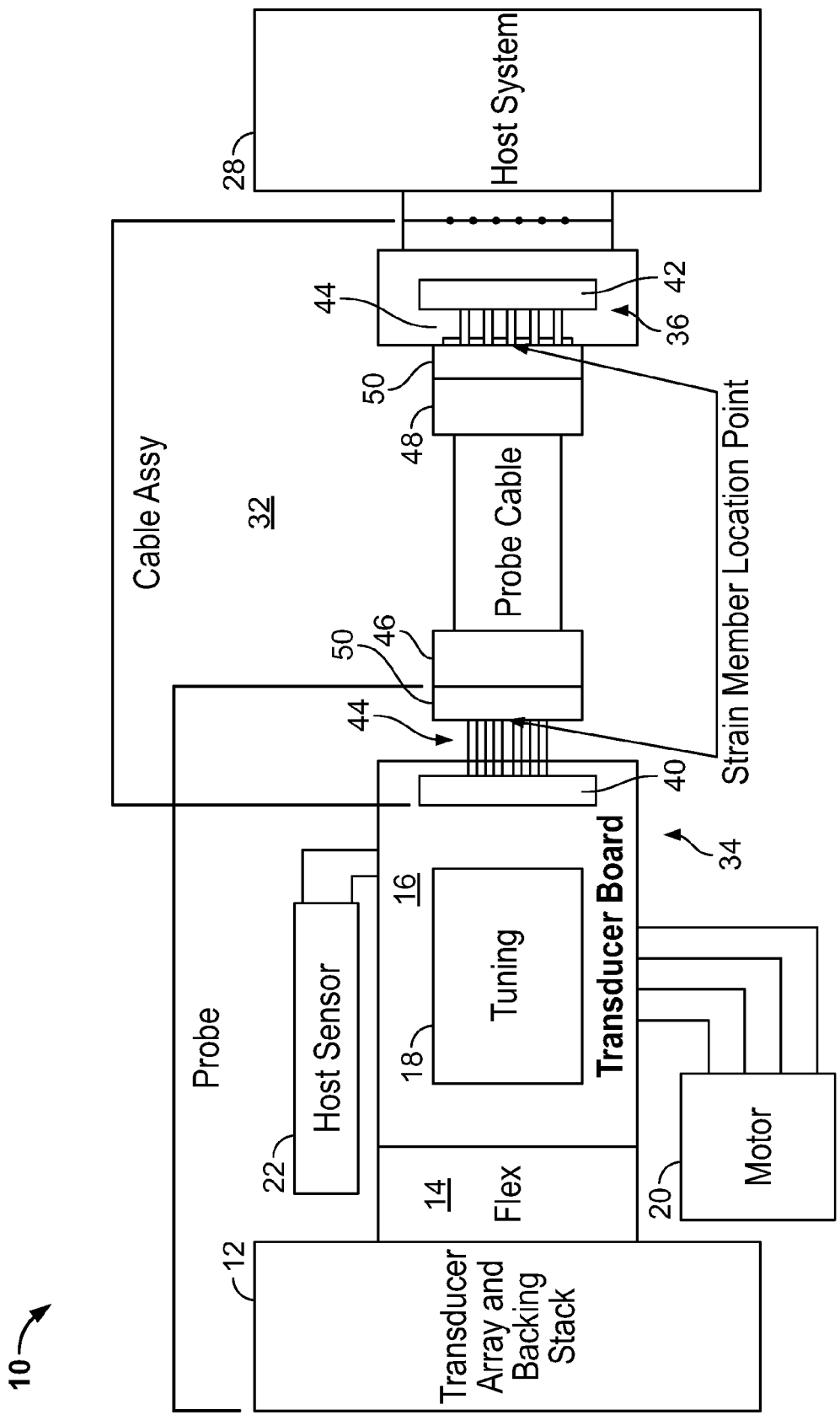
FIG. 1 is a block diagram of an ultrasound probe formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Described herein are various embodiments for a connector assembly. The connector assembly includes a strain relief assembly that is aligned such that the pull force of the strain relief assembly is proximately aligned with a centerline of the system cable. The strain relief assembly may be assembled and disassembled without the need for spare parts and may be utilized with a variety of different ultrasound probes.

Various embodiments described herein may be implemented with an ultrasound probe 10 as shown in FIG. 1. More specifically, FIG. 1 is a block diagram of an exemplary ultrasound probe that is constructed in accordance with various embodiments. The ultrasound probe 10 includes a transducer array and backing stack 12 (the "transducer array 12"), a plurality of transducer flex cables 14, which may be formed as a scan head cable, and a transducer board 16 that support processing electronics. The processing electronics may include, for example, a tuning circuit 18 for providing impedance tuning from the transducer array 12 to the cable of each channel. In various embodiments, the tuning circuit 18 may be implemented as a passive inductor. The ultrasound probe 10 may also include a motor 20 that is utilized to position the transducer array 12 in various operational configurations. The ultrasound probe 10 may further include a Hall effect sensor 22 that is utilized to In operation, the ultrasound probe communicates with a host system 28 via a system cable 32. The system cable 32 may be embodied as a coaxial cable having a first end 34 that is configured to couple to the ultrasound probe 10 and a second end 36 that is configured to couple to the host system 28. More specifically, the system cable 32 includes a connector 40 that is disposed proximate to the first end 34 and is utilized to couple the system cable 32 to the ultrasound probe 10. Moreover, the system cable 32 includes a second connector 42 that is disposed proximate to the second end 36 and is utilized to couple the system cable 32 to the host system 28. In various embodiments, the system cable 32 includes a plurality of coaxial cables 44 that connect the ultrasound probe 10 to the host system 28. The system cable 32 also includes a first flex relief device 46 that is coupled proximate to the first end 34 and a second flex relief device 48 that is coupled proximate to the second end 36. The system cable 32 further includes a pair of connectors 50 that are discussed in more detail below.

Figure 2:
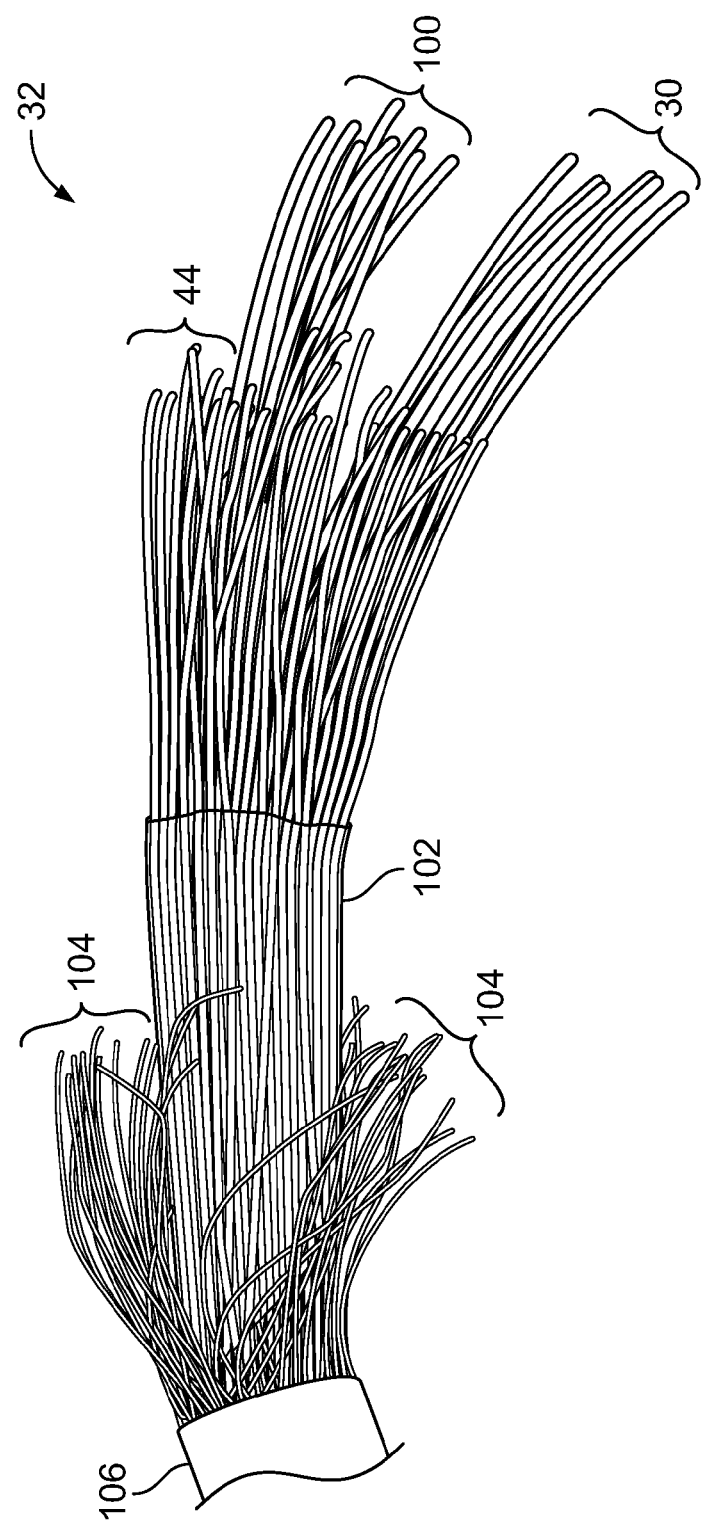
FIG. 2 is a side view of a portion of the system cable shown in FIG. 1 with a portion of the jacket removed.

FIG. 2 is a side perspective view of a portion of the system cable 32 shown in FIG. 1. In various embodiments, the system cable 32 includes the plurality of coaxes 44, also referred to herein as inner conductors, and may include other cables, such as for example, the communication line 30. Each coax 44 may be formed to include a central conductor (not shown) and a flexible insulating sheath (not shown) that surrounds the central conductor. The system cable 32 further includes a strain member 100. The strain member 100 is generally disposed along a longitudinal axis of the system cable 32 and generally located at a center point of the system cable 32. Thus, in the exemplary embodiment, the strain member 100 is disposed radially inwardly from the plurality of coaxes 44 such that the coaxes 44 substantially circumscribe the strain member 100. In various embodiments, the strain member 100 may be fabricated from, for example, a single strand of Kevlar or Aramid material. Optionally, the strain member 100 may be fabricated from a plurality of strands of Kevlar or Aramid material. In further embodiments, the strain member 100 may be fabricated from any suitable non-conductive material.

The system cable 32 may also include a supporting member such as a tape 102 that substantially circumscribes the strain member 100, the coaxes 44, and the communication line 30. In operation, the tape 102 facilitates securing the coaxes 44, the communication line 30 and the strain member 100 in a substantially fixed position with respect to each other. The system cable 32 further includes a shield 104 and a jacket 106. The shield 104, also referred to herein as an outer conductor, may be embodied as a tubular conducting shield that may be fabricated using a plurality of metallic wires that are braided together to form the shield 104. The jacket 106 is a tubular jacket that encases the shield 104 and the various other components located internally within the jacket 106. In various embodiments, the jacket 106 is fabricated using a flexible insulating material. In operation, the system cable 32 conducts electrical signals using the inner conductors while the outer conductor or shield 104 is kept at ground potential. Accordingly, a voltage is applied across the inner conductors and the outer conductor or shield 104 to carry the electrical signals.

Figure 3:
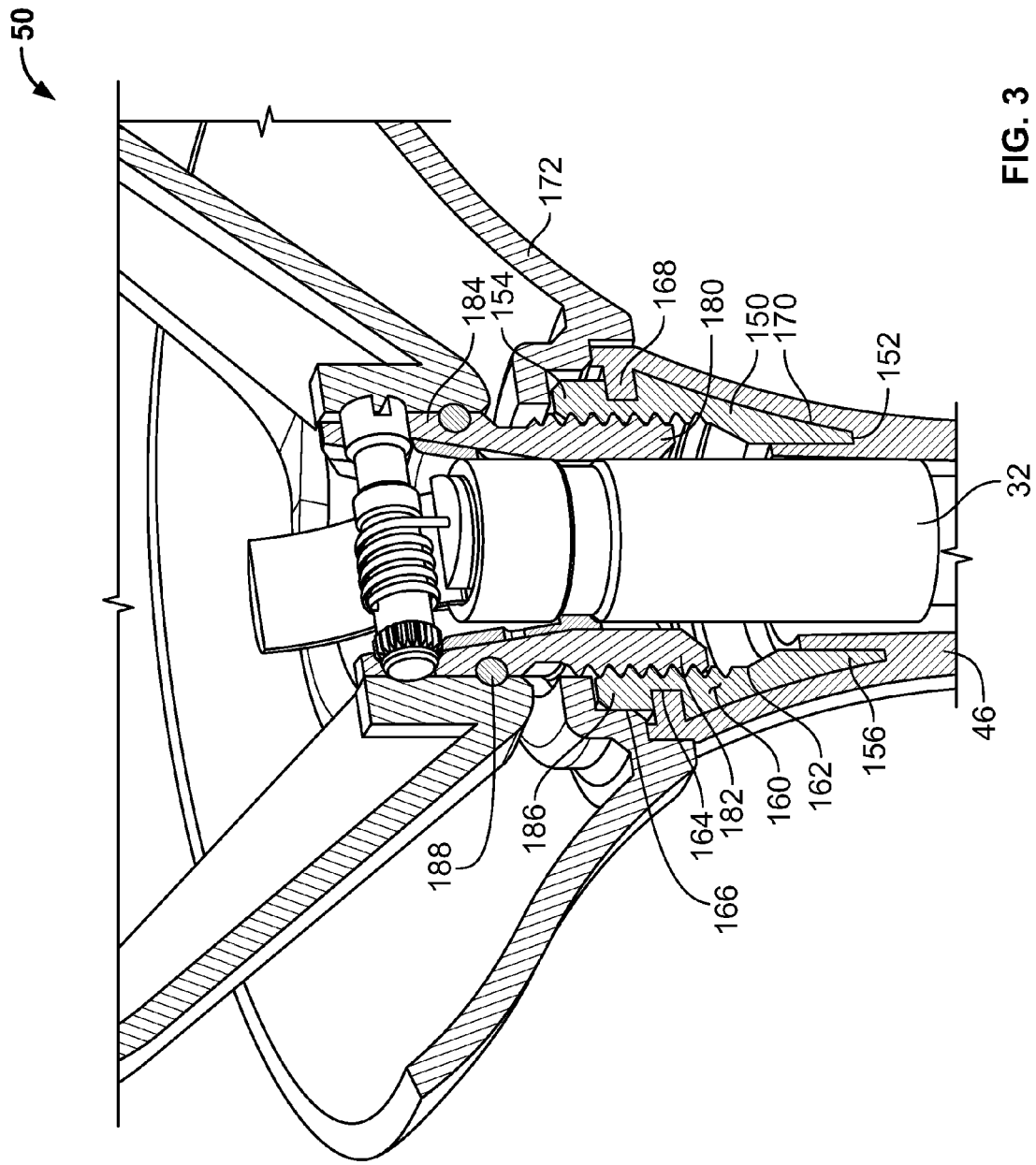
FIG. 3 is a cross-sectional view of an exemplary connector that may be formed in accordance with various embodiments.
Figure 4:
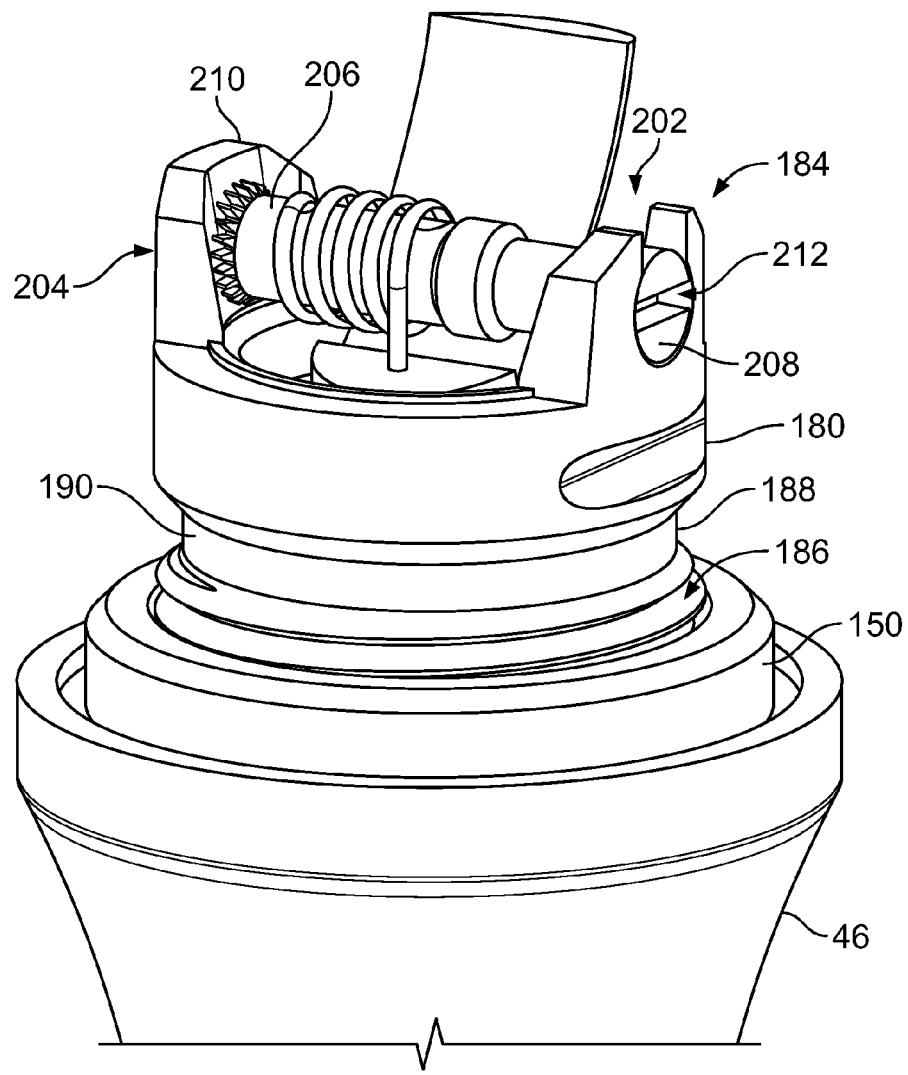
FIG. 4 is a side perspective view of the exemplary connector shown in FIG. 3.

FIG. 3 is a side cut-away view of the exemplary connector 50 that is utilized to couple the system cable 32 to the ultrasound probe 10 as shown in FIG. 1. FIG. 4 is a side view of the connector 50 shown in FIG. 3 after assembly of the connector 50. In various embodiments, the connector 50 is fabricated using a non-conductive material, such as for example, a plastic material. Optionally, portions of the connector 50 may be fabricated from materials other than plastic. The connector 50 includes a substantially cylindrical cable clamp 150. The cable clamp 150 is hollow to form and opening that is sized to receive the system cable 32 therethrough. The cable clamp 150 has a first end 152 and an opposite second end 154. The first end 152 forms a ferrule 156 that is configured to be inserted into an opening formed in the flex relief device 46. In operation, the flex relief device 46 is secured around the system cable 32 and provides support to the system cable 32 to facilitate preventing the system cable 32 from being flexed beyond a point that may result in damage to the various conductors housed within the system cable 32. Moreover, the ferrule 156 is generally formed as a cylindrical device, having an opening at each end that is attached to system cable 32 and configured to protect the system cable 32 from fraying or other damage.

The cable clamp second end 154 is formed to include a plurality of threads 160. In the exemplary embodiment, the threads 160 are formed on an inner surface 162 of the cable clamp 150 proximate to the second end 154. Thus, in the exemplary embodiment, the inner surface 162 gradually tapers from the threads 160 to the first end 152 to form the ferrule portion 156 of the cable clamp 150. The cable clamp 150 also includes a slot 164 that is formed in an outer surface 166 of the cable clamp 150. In the exemplary embodiment, the slot 164 extends radially around the outer surface 166 and is disposed radially outwardly from the threads 160. To secure the cable clamp 150 to the flex relief device 46, the flex relief device 46 includes a tab 168 that extends radially around an inner surface 170 of the flex relief device 46. Accordingly, during assembly, the cable clamp 150 is positioned such that the ferrule 156 extends at least partially into the flex relief device 46. The flex relief device 46 is then expanded to enable the tab 168 to be inserted into the slot 164. Thus, the combination of the tab 168 and the slot 164 enables the cable clamp 150 to be secured to the flex relief device 46. In various embodiments, a user may utilize a tool or fixture 172 to facilitate expanding the flex relief device 46 and thus enable the tab 168 to be inserted into the slot 164.

The connector 50 also includes a collet 180. The collet 180 is generally formed as a cylindrical sleeve that is configured to circumscribe the system cable 32 and facilitated securing the system cable 32 in a fixed position. The collet 180 includes a first end 182 and a second end 184. In various embodiments, the collet first end 182 includes a plurality of threads 186 that are formed on an external surface 188 of the collet 180. The collet 180 may also include a slot 190 that is formed in the external surface 188 of the collet 180. In the exemplary embodiment, the slot 190 extends radially around the external surface 188 and is disposed radially proximate to the second end 184. During assembly, the collet 180 is positioned such that the collet threads 186 are substantially aligned with the threads 160 formed in the cable clamp 150. A tool or fixture 192 is then utilized to thread the collet 180 into the cable clamp 150. In various other embodiments, described below, the collet 180 may have a tapered shape and may be secured to the cable clamp 150 using a clip.

In various embodiments, and as shown in FIG. 4, the collet 180 further includes a strain relief assembly 200 that functions as a winch and is formed integrally with the collet 180. Accordingly, the collet second end 184 includes a slot 202 and an opening 204. The slot 202 is disposed on an opposite side of the collet 180 from the opening 204. In various embodiments, the slot 202 has a substantially C-shape and the opening 204 is substantially circular. The slot 202 is flexible to enable an arbor 206 to be inserted therein. More specifically, the arbor 206 has a first end 208 that is configured to be secured within the slot 202. The arbor 206 also has a second end 210 that is configured to be secured within the opening 204.

During assembly, the arbor first end 208 is inserted into the opening 204. Moreover, the arbor second end 210 is depressed into the slot 202. The pressure applied to the arbor second end 210 causes the sides of the C-shaped slot to expand. Continued pressure enables the arbor second end 210 to be depressed within the slot 202. After the arbor second end 210 is fully inserted within the slot 202, the sides of the slot 202 contact to secure the arbor 206 to the collet 180. Thus, the combination of the slot 202 and the opening 204 enable the arbor 206 to be secured to the collet 180 and also remain rotatable with respect to the collet 180. In various embodiments, the arbor first end 208 and/or the arbor second end 210 may have a slot 212 formed therein. During assembly, the slot 212 enables the arbor 206 to be rotated with respect to the collet 180.

Figure 5:
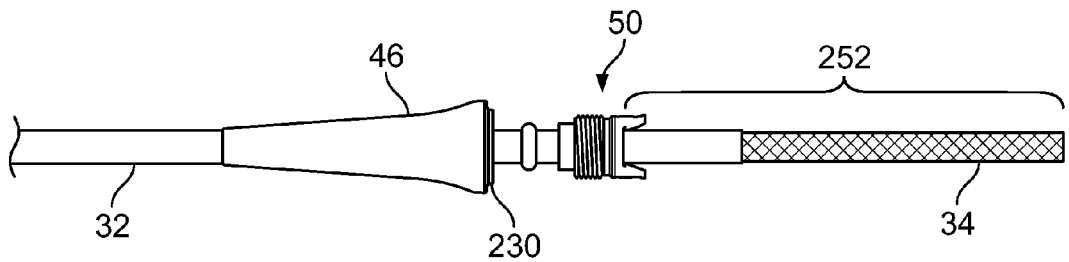
FIG. 5 is a side view of an exemplary system cable in an initial assembly stage.

FIG. 5 to FIG. 9 are side views of the system cable 32 is a various stages of assembly in accordance with various embodiments described herein. For example, as shown in FIG. 5, initially the first end 34 of the system cable 32 is inserted through the flex relief device 46. An o-ring 250 is then placed around the system cable 32 and the cable clamp 150, which forms a portion of the connector 50, is placed on the system cable 32 such that the o-ring 250 is disposed between the flex relief device 46 and the cable clamp 150. In various embodiments, the system cable 32 is inserted though the flex relief device 46, the o-ring 250 and the cable clamp 150 such that a portion 252 of the system cable 32 extends past the connector 50 as shown in FIG. 5. In operation, the o-ring 250 facilitates inhibiting fluids from entering either the system cable 32 or the ultrasound probe 10.

Figure 6:
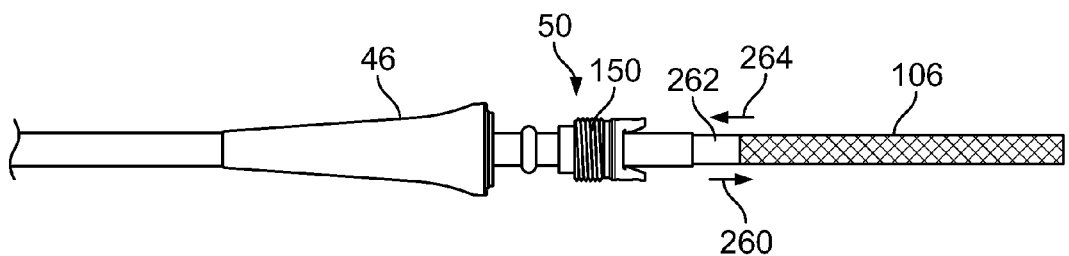
FIG. 6 is a side view of the exemplary system cable shown in FIG. 5 in a subsequent assembly stage.

As shown in FIG. 6, the jacket 106 is moved in a direction 260. A section of shrink tube 262 is then disposed over a portion of the system cable 32. The jacket 106 is then moved in a direction 264 such that the jacket 106 substantially covers the shrink tube 262.

Figure 7:
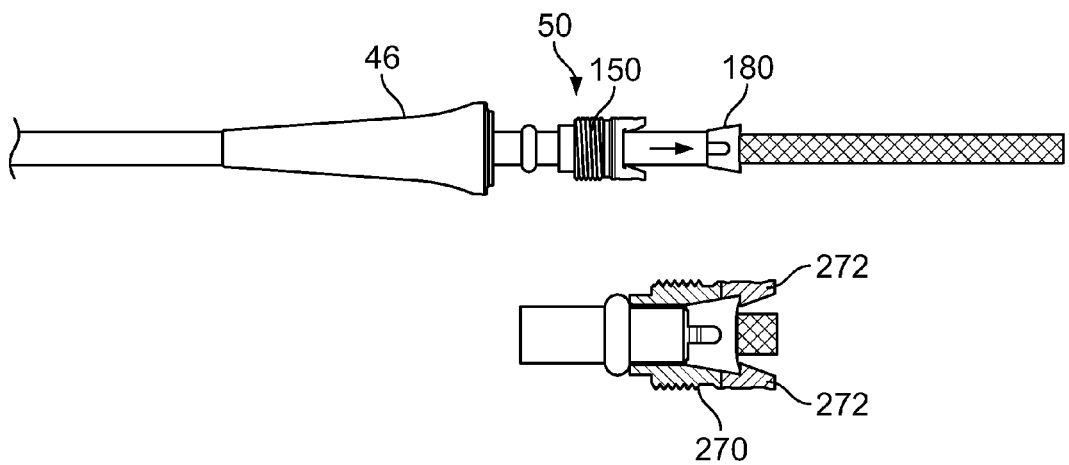
FIG. 7 is a side view of the exemplary system cable shown in FIG. 5 in another subsequent assembly stage.

As shown in FIG. 7, the collet 180 is placed around the system cable 32 and coupled with the cable clamp 150. As discussed above, the collet 180 may be secured to the cable clamp 150 using the collet threads 186 and the threads 160 formed in the cable clamp 150. A tool or fixture 192 is then utilized to thread the collet 180 into the cable clamp 150. In various other embodiments, the collet 180 may be secured to the cable claim 150 using a clip 270. More specifically, the clip 270 includes a pair of tabs 272 that are configured to engage and secure the collet 180 to the cable clamp 150. Accordingly, during assembly, a user may depress the pair of tabs 272, position the collet 180 at least partially over the cable clamp 150, and the release the tabs 272. Thus, the tabs 272, in a relaxed position, facilitate locking the collet in a predetermined position.

Figure 8:
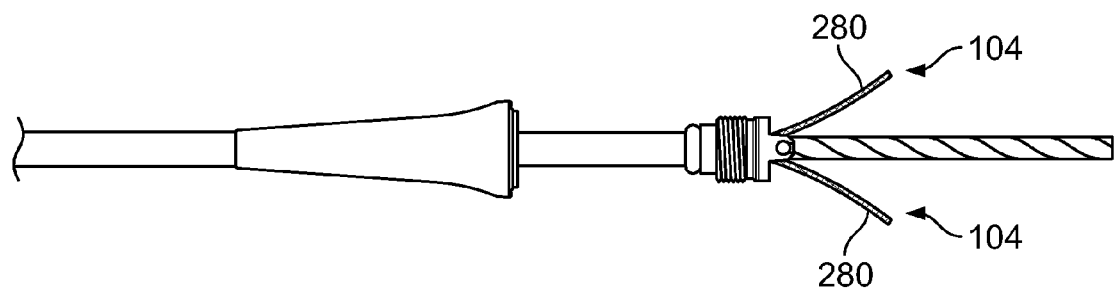
FIG. 8 is a side view of the exemplary system cable shown in FIG. 5 in another subsequent assembly stage.

As shown in FIG. 8, the shield 104 is separated into at least two shield portions 280. Thus, in various embodiments, each shield portion 280 includes a plurality of shield wires that are twisted to together to form a bundle.

Figure 9:
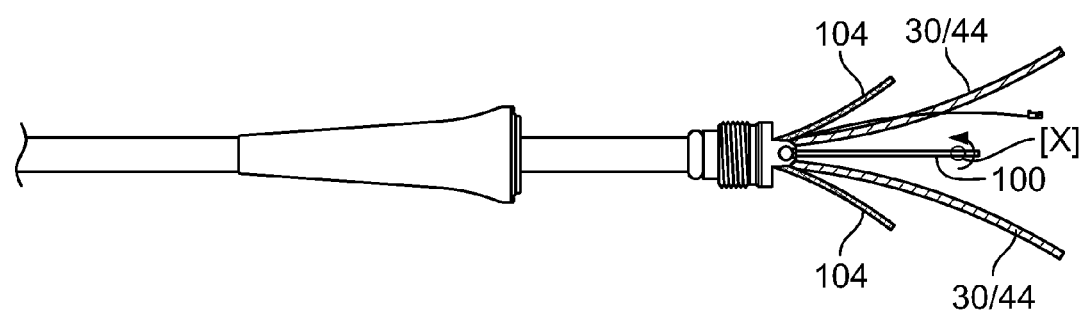
FIG. 9 is a side view of the exemplary system cable shown in FIG. 5 in another subsequent assembly stage.
Figure 10:
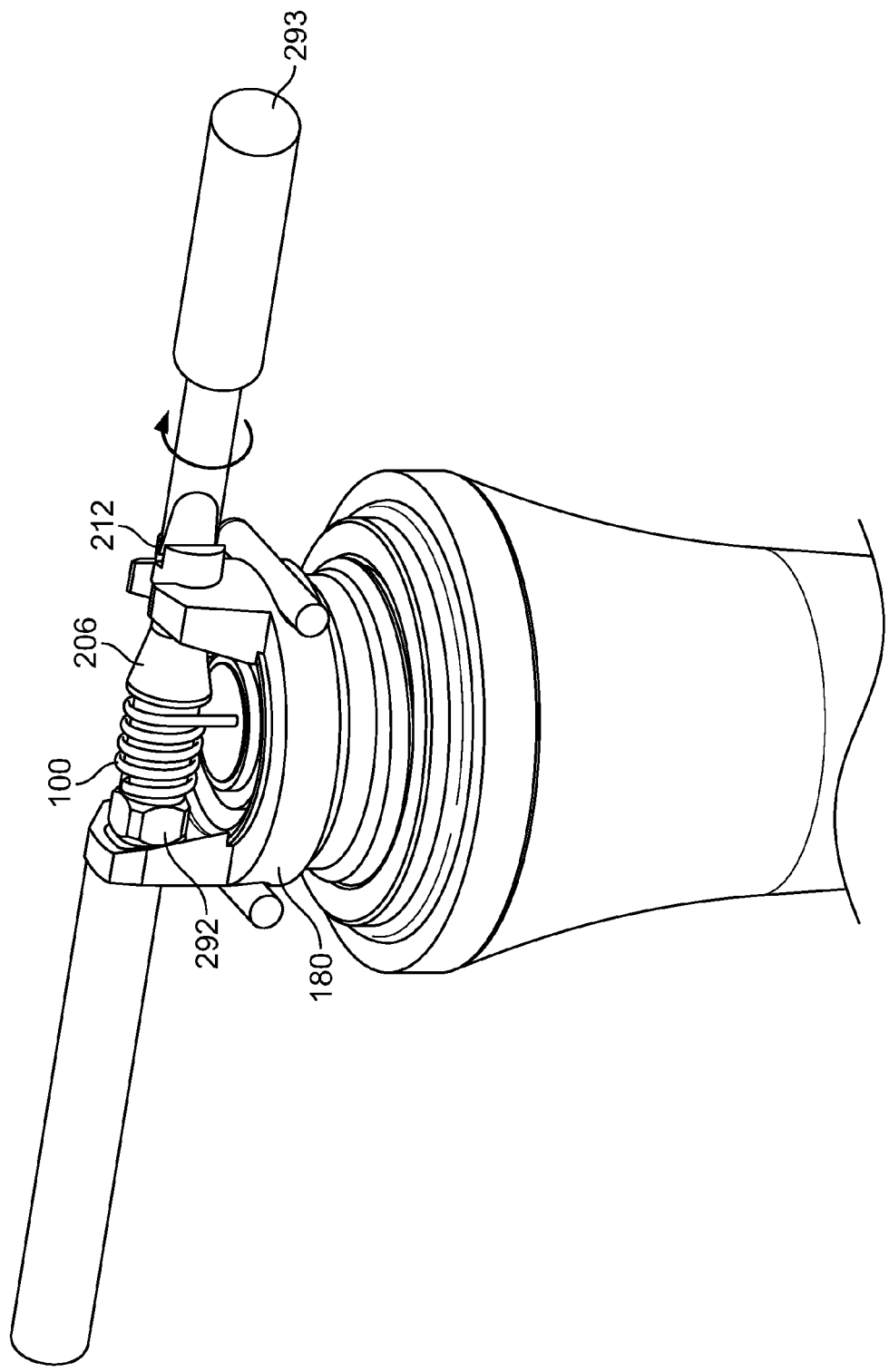
FIG. 10 is a side view of the exemplary system cable shown in FIG. 5 in still another subsequent assembly stage.

As shown in FIG. 9, the plurality of coax cables 44 and/or communication lines 30 are separated from the strain member 100 to expose the strain member 100. The end of the strain member 100 is then at least partially wrapped around the arbor 206. The arbor 206 is then operated to apply tension to the strain member 100. More specifically, as discussed above, the arbor 206 includes the slot 212. Accordingly, to increase the tension on the strain member 100, a tool 290, such as a screw driver, may be inserted into the slot 212. The tool 290 is then rotated in a clockwise or counter-clockwise direction to either increase or decrease the tension on the strain member 100. After the strain member 100 has been adjusted to a predetermined tension, an adhesive (not shown) may be applied to a surface of the arbor 206 to secure the strain member 100 to the arbor 206. Moreover, to facilitate preventing the arbor 206 from moving after the predetermined strain has been achieved, the arbor 206 may include a locking device 292. The locking device 292 may be embodied as a protrusion that is formed on the arbor 206 that is configured to interlock with the opening formed on the collet 180.

In operation, the strain relief assembly 200, which includes the arbor 206 and the associated openings and slots in the collet 180 allow for flexible length adaption of the strain member 100 to ensure the fibers forming the strain member 100 are tensioned for proper functionality. Moreover, because the strain member 100 is centrally located within the system cable 32, the strain relief assembly 200 is aligned such that the pull force of the arbor 206 is also in the center of the system cable 32. The strain relief assembly 200 may be assembled and disassembled without the need for spare parts. Moreover, by bending the coaxes cables 44 sideways at the point where the connector 50 couples to the system cable 32, the connector 50 may be moved through relatively small openings which allow the connector to be assembled at the point where the coax cables 44 terminate.

The connector described herein may be fabricated using, for example, plastic parts. Moreover, the connector may be utilized with different ultrasound probes and thus may provide increased logistic advantages over conventional connectors. More specifically, the connector described herein may be customized for specific ultrasound probes after cable assembly by allowing for assembly to probe specific parts such as for example, a plastic housing after coax cable termination.

Figure 11:
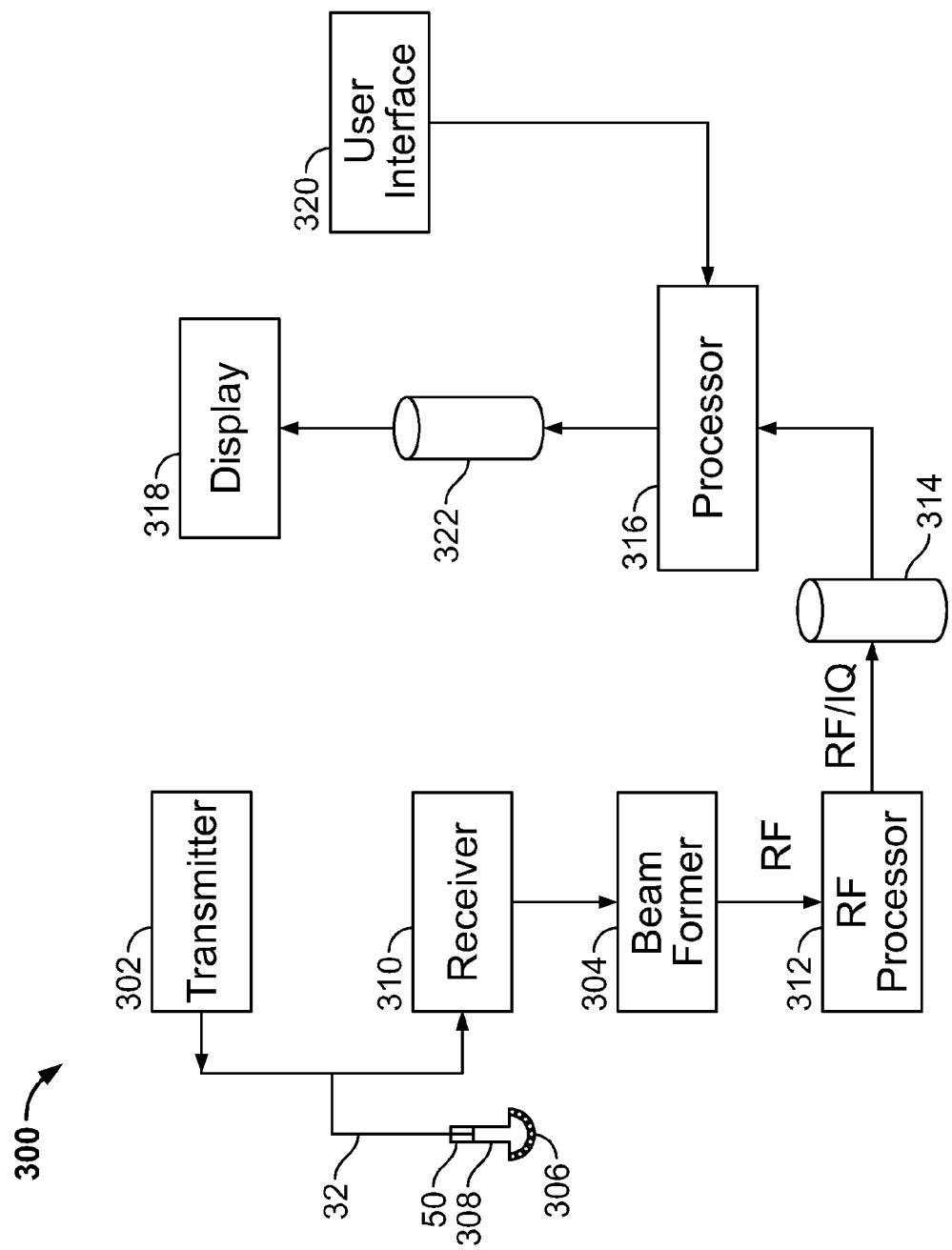
FIG. 11 is a block diagram of an exemplary medical imaging system formed in accordance with various embodiments.

Various embodiments described herein may be implemented in an ultrasound system such as the ultrasound system 300 as shown in FIG. 11. More specifically, FIG. 11 is a block diagram of an exemplary ultrasound imaging system 300 that is constructed in accordance with various embodiments. The ultrasound system 300 is capable of electrical or mechanical steering of a soundbeam (such as in 3D space) and is configurable to acquire information (e.g., image slices) corresponding to a plurality of 2D representations or images of a region of interest (ROI) in a subject or patient, which may be defined or adjusted as described in more detail herein. The ultrasound system 300 is configurable to acquire 2D images in one or more planes of orientation. The ultrasound system 300 may be embodied in a small-sized system, such as laptop computer, a portable imaging system, a pocket sized system as well as in a larger console-type system.

The ultrasound system 300 includes a transmitter 302 that, under the guidance of a beamformer 304, drives an array of elements 306 (e.g., piezoelectric elements) within a probe 308 to emit pulsed ultrasonic signals, i.e. sound waves, into a body. A variety of geometries may be used. As shown in FIG. 11, the probe 308 may be coupled to the transmitter 302 via the system cable 32 and the connector 50. The sound waves are back-scattered from structures in the body, like blood cells flowing through a blood vessel, to produce echoes that return to the elements 306. The echoes are received by a receiver 310. The received echoes are passed through the beamformer 304, which performs receive beamforming and outputs an RF signal. The RF signal then passes through an RF processor 312. Optionally, the RF processor 312 may include a complex demodulator (not shown) that demodulates the RF signal to form IQ data pairs representative of the echo signals. The RF or IQ signal data may then be routed directly to a buffer 314 for storage.

In the above-described embodiment, the beamformer 304 operates as a transmit and receive beamformer. Optionally, the probe 308 includes a 2D array with sub-aperture receive beamforming inside the probe 308. The beamformer 304 may delay, apodize and/or sum each electrical signal with other electrical signals received from the probe 308. The summed signals represent echoes from the ultrasound beams or lines. The summed signals are output from the beamformer 304 to the RF processor 312. The RF processor 312 may generate different data types, e.g. B-mode, color Doppler (velocity/power/variance), tissue Doppler (velocity), and Doppler energy, for multiple scan planes or different scanning patterns. For example, the RF processor 312 may generate blood flow Doppler data for multi-scan planes. The RF processor 312 gathers the information (e.g. I/Q, B-mode, color Doppler, tissue Doppler, and Doppler energy information) related to multiple data slices and stores the data information, which may include time stamp and orientation/rotation information, in the buffer 314.

The ultrasound system 300 also includes a processor 316 to process the acquired ultrasound information (e.g., RF signal data or IQ data pairs) and prepare frames of ultrasound information for display on a display 318. The processor 316 is adapted to perform one or more processing operations according to a plurality of selectable ultrasound modalities on the acquired ultrasound data. Acquired ultrasound data may be processed and displayed in real-time during a scanning session as the echo signals are received. Additionally or alternatively, the ultrasound data may be stored temporarily in the buffer 314 during a scanning session and then processed and displayed in an off-line operation.

The processor 316 is connected to a user interface 320 that may control operation of the processor 316 as explained below in more detail. The display 318 may include one or more monitors that present patient information, including diagnostic ultrasound images to the user for diagnosis and analysis. The buffer 314 and/or a memory 322 may store two-dimensional (2D) or three-dimensional (3D) data sets of the ultrasound data, where such 2D and 3D data sets are accessed to present 2D (and/or 3D images). The images may be modified and the display settings of the display 318 may also be manually adjusted using the user interface 320.

Figure 12:
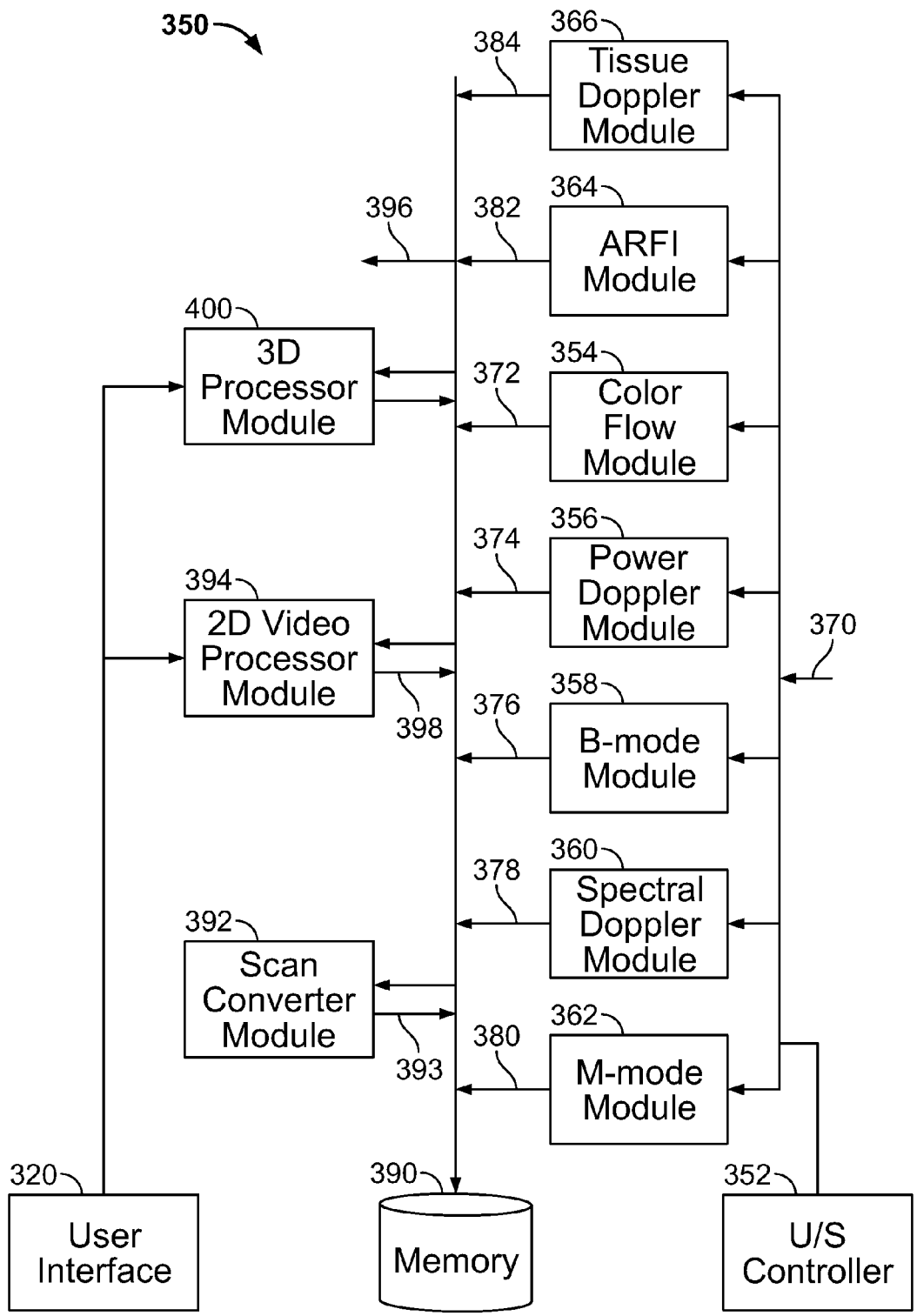
FIG. 12 is a block diagram illustrating a portion of the imaging system shown in FIG. 11 in accordance with various embodiments.

The various components of the ultrasound system 300 may have different configurations. For example, FIG. 12 illustrates an exemplary block diagram of an ultrasound processor module 350, which may be embodied as a portion of the processor 316 shown in FIG. 11. The ultrasound processor module 350 is illustrated conceptually as a collection of sub-modules, but may be implemented utilizing any combination of dedicated hardware boards, DSPs, processors, etc. Alternatively, the sub-modules of FIG. 12 may be implemented utilizing an off-the-shelf PC with a single processor or multiple processors, with the functional operations distributed between the processors. As a further option, the sub-modules of FIG. 12 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 12 may be controlled by a local ultrasound controller 352 or by the processor 316. The sub-modules 354-366 perform mid-processor operations. The ultrasound processor module 350 may receive ultrasound data 370 in one of several forms. In the embodiment of FIG. 12, the received ultrasound data 370 constitutes I,Q data pairs representing the real and imaginary components associated with each data sample. The I,Q data pairs are provided to one or more of a color-flow sub-module 354, a power Doppler sub-module 356, a B-mode sub-module 358, a spectral Doppler sub-module 360 and an M-mode sub-module 362. Optionally, other sub-modules may be included such as an Acoustic Radiation Force Impulse (ARFI) sub-module 364 and a Tissue Doppler (TDE) sub-module 366, among others.

Each of sub-modules 354-366 are configured to process the I,Q data pairs in a corresponding manner to generate color-flow data 372, power Doppler data 374, B-mode data 376, spectral Doppler data 378, M-mode data 380, ARFI data 382, and tissue Doppler data 384, all of which may be stored in a memory 390 (or memory 314 or memory 322 shown in FIG. 11) temporarily before subsequent processing. For example, the B-mode sub-module 358 may generate B-mode data 376 including a plurality of B-mode image planes.

The data 372-484 may be stored, for example, as sets of vector data values, where each set defines an individual ultrasound image frame. The vector data values are generally organized based on the polar coordinate system.

A scan converter sub-module 392 accesses and obtains from the memory 390 the vector data values associated with an image frame and converts the set of vector data values to Cartesian coordinates to generate an ultrasound image frame 393 formatted for display. The ultrasound image frames 393 generated by the scan converter module 392 may be provided back to the memory 390 for subsequent processing or may be provided to the memory 314 or 322.

Once the scan converter sub-module 392 generates the ultrasound image frames 393 associated with, for example, B-mode image data, and the like, the image frames 393 may be restored in the memory 390 or communicated over a bus 396 to a database (not shown), the memory 314, and the memory 322 and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display 318 (shown in FIG. 11), which may include one or more monitors or windows of the display, to display the image frame. The image displayed in the display 318 is produced from image frames of data in which each datum indicates the intensity or brightness of a respective pixel in the display.

Referring again to FIG. 12, a 2D video processor sub-module 394 combines one or more of the frames generated from the different types of ultrasound information. For example, the 2D video processor sub-module 394 may combine a different image frames by mapping one type of data to a grey map and mapping the other type of data to a color map for video display. In the final displayed image, color pixel data may be superimposed on the grey scale pixel data to form a single multi-mode image frame 398 (e.g., functional image) that is again re-stored in the memory 390 or communicated over the bus 396. Successive frames of images may be stored as a cine loop in the memory 390 or memory 390. The cine loop represents a first in, first out circular image buffer to capture image data that is displayed to the user. The user may freeze the cine loop by entering a freeze command at the user interface 320. The user interface 320 may include, for example, a keyboard and mouse and all other input controls associated with inputting information into the ultrasound system 300 (shown in FIG. 11).

A 3D processor sub-module 400 is also controlled by the user interface 320 and accesses the memory 390 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

The various embodiments and/or components, for example, the modules, or components and controllers therein, such as of the imaging system 300, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A connector assembly for coupling an coaxial cable to an ultrasound probe, said connector assembly comprising:
   a cable clamp having an opening extending therethrough, the opening sized to receive a coaxial cable therethrough, the coaxial cable including a strain member and a plurality of coaxial cables extending therethrough; and
   a collet configured to couple to the cable clamp, the collet including an arbor that is configured to tension the strain member to a predetermined tension.

2. The connector assembly of claim 1, wherein the collet is threadably coupled to the cable clamp.

3. The connector assembly of claim 1, wherein the collet is coupled to the cable clamp using a clip assembly.

4. The connector assembly of claim 1, wherein the cable clamp and the collect are fabricated from a plastic material.

5. The connector assembly of claim 1, wherein the cable clamp comprises a ferrule that is configured to couple to a flexible relief device.

6. The connector assembly of claim 1, wherein the collet includes an opening and a slot, a first end of the arbor configured to insert into the opening and a second end of the arbor configured to insert into the slot.

7. The connector assembly of claim 1, wherein the arbor is rotatable with respect to the collet to tension the strain member to the predetermined tension.

8. The connector assembly of claim 1, further comprising an adhesive to couple the strain member to the arbor.

9. The connector assembly of claim 1, further comprising a locking device to secure the arbor at the predetermined tension.

10. The connector assembly of claim 1, wherein the cable clamp comprises a slot formed therein, the slot being configured to receive a tab therein to couple the cable clamp to a flexible relief device.

11. The connector assembly of claim 1, wherein the plurality of coaxial cables extend between the arbor and the cable clamp.

12. A method of fabricating a coaxial cable assembly, said method comprising:
   inserting a coaxial cable through a cable clamp, the coaxial cable including a strain member and a plurality of coaxial cables extending therethrough;
   inserting the coaxial cable through a collet, the collet including an arbor;
   coupling the collet to the cable clamp;
   coupling the strain member to the arbor; and
   rotating the arbor to tension the strain member to a predetermined tension.

13. The method of claim 12, further comprising threadably coupling the cable clamp to the collet.

14. The method of claim 12, further comprising coupling the cable clamp to the collet using a clip assembly.

15. The method of claim 12, wherein the cable clamp and the collect are fabricated from a plastic material.

16. The method of claim 12, wherein the cable clamp comprises a ferrule that is configured to couple to a flexible relief device.

17. The method of claim 12, wherein the collet includes an opening and a slot, the method further comprising inserting a first end of the arbor into the opening and a second end of the arbor into the slot.

18. An ultrasound imaging system comprising:
   an ultrasound probe;
   a system cable coupled between the ultrasound probe and a host system; and
   a connector assembly for coupling the ultrasound probe to the system cable, the connector assembly including
      a cable clamp having an opening extending therethrough, the opening sized to receive the system cable therethrough, the system cable including a strain member and a plurality of coaxial cables extending therethrough; and
      a collet configured to couple to the cable clamp, the collet including an arbor that is configured to tension the strain member to a predetermined tension.

19. The ultrasound imaging system of claim 18, wherein the cable clamp and the collect are fabricated from a plastic material.

20. The ultrasound imaging system of claim 18, wherein the cable clamp comprises a ferrule that is configured to couple to a flexible relief device.

* * * * *